(12) United States Patent
Sugiuchi

(10) Patent No.: US 6,794,157 B1
(45) Date of Patent: Sep. 21, 2004

(54) METHODS FOR FRACTIONAL QUATIFICATION OF CHOLESTEROL IN LIPOPROTEINS AND QUANTIFICATION REAGENTS

(75) Inventor: Hiroyuki Sugiuchi, Kumamoto (JP)

(73) Assignee: Kyowa Medex Co., Ltd., Tokyo (JP)

( * ) Notice: Subject to any disclaimer, the term of this patent is extended or adjusted under 35 U.S.C. 154(b) by 0 days.

(21) Appl. No.: 09/787,393

(22) PCT Filed: Jul. 30, 1999

(86) PCT No.: PCT/JP99/04128

§ 371 (c)(1),
(2), (4) Date: Mar. 19, 2001

(87) PCT Pub. No.: WO00/17388

PCT Pub. Date: Mar. 30, 2000

(30) Foreign Application Priority Data

Sep. 18, 1998 (JP) .......................... 10/264367

(51) Int. Cl.[7] ................................. C12Q 1/60
(52) U.S. Cl. .................... 435/11; 435/19; 435/26
(58) Field of Search .................. 435/11, 19, 26; 436/71

(56) References Cited

U.S. PATENT DOCUMENTS

| | | | |
|---|---|---|---|
| 4,892,815 A | | 1/1990 | Kerscher et al. ............. 435/7 |
| 5,691,159 A | | 11/1997 | Miyauchi et al. ............ 435/11 |
| 5,773,304 A | * | 6/1998 | Hino et al. ................. 436/174 |
| 5,804,450 A | * | 9/1998 | Karl ........................... 436/71 |
| 5,879,901 A | * | 3/1999 | Futatsugi et al. ............ 435/11 |
| 5,888,755 A | | 3/1999 | Miyauchi et al. ............ 435/11 |
| 5,925,534 A | * | 7/1999 | Miki et al. .................. 435/11 |
| 6,333,166 B1 | * | 12/2001 | Nakamura et al. ........... 435/11 |

FOREIGN PATENT DOCUMENTS

| | | |
|---|---|---|
| EP | 753 583 | 1/1997 |
| EP | 763 741 | 3/1997 |
| JP | 06-242110 | 9/1994 |
| JP | 8-131197 | 5/1996 |

OTHER PUBLICATIONS

Sugiuchi, H., Clinical Chemistry, vol. 44, No. 3, pp. 522–531 (1998).

Sugiuchi, "Direct Measurement of High–Density Lipoprotein . . . ", Clinical Chemistry, vol. 41, No. 5, pp. 717–723 (1995).

Sugiuchi, "Simultanous Automated Determination of HDL Cholesterol . . . ", Clinical Chemistry and Laboratory Medicine, vol. 37, Spec. Suppl. p. S726 (Abstract XP001018228).

* cited by examiner

*Primary Examiner*—Ralph Gitomer
(74) *Attorney, Agent, or Firm*—Fitzpatrick, Cella, Harper & Scinto

(57) ABSTRACT

The present invention provides a method for the quantitative determination of cholesterol in low density lipoproteins and a reagent kit for use therein. The present invention also provides a method for continuous fractional determination of cholesterol in high density lipoproteins and cholesterol in low density lipoproteins and a reagent kit for use therein, as well as a method for continuous fractional determination of cholesterol in high density lipoproteins and total cholesterol and a reagent kit for use therein.

31 Claims, 3 Drawing Sheets

METHODS FOR FRACTIONAL QUATIFICATION OF CHOLESTEROL IN LIPOPROTEINS AND QUANTIFICATION REAGENTS

This application is a National Stage of International Application No. PCT/JP99/04128 filed Jul. 30, 1999.

TECHNICAL FIELD

The present invention relates to a method for the quantitative determination of cholesterol in low density lipoproteins (LDL) (hereinafter referred to as LDL cholesterol), which is important in the field of clinical diagnosis, and a reagent for use in the method. The present invention also relates to a method for the continuous fractional determination of cholesterol in high density lipoproteins (HDL) (hereinafter referred to as HDL cholesterol) and LDL cholesterol, which are also important in the field of clinical diagnosis, and a reagent kit for use therein. The present invention further relates to a method for the continuous fractional determination of HDL cholesterol, LDL cholesterol and total cholesterol [the term is used to mean total cholesterol in HDL, LDL, very low density lipoproteins (hereinafter referred to as VLDL) and chylomicron (hereinafter referred to as CM)], which are important in the field of clinical diagnosis, as well as a reagent kit to be used therefor.

BACKGROUND ART

In general, HDL is called good cholesterol since HDL functions to remove cholesterol accumulated on arterial walls and transport cholesterol to liver. On the other hand, LDL is generally termed bad cholesterol because of its action to transport cholesterol to peripheral tissues including arterial walls. In the field of clinical investigations, the levels of HDL cholesterol, LDL cholesterol and total cholesterol are useful indices for total judgement of lipid-related diseases such as arteriosclerosis, etc.

These cholesterol levels are separately determined using reagents exclusively specific to each type of cholesterol so that an autoanalyzer is designed so as to be suitable for individual determination of these cholesterol levels. It has been desired to further improve the specificity of a reagent to each cholesterol. Besides, no simple and automated method for the continuous fractional determination of HDL cholesterol, LDL cholesterol, total cholesterol, etc in the same detection system is known.

DISCLOSURE OF THE INVENTION

An object of the present invention is to provide a method for the quantitative determination of LDL cholesterol and a determination reagent for use in such a method.

Another object of the present invention is to provide a method for the continuous fractional determination of HDL cholesterol and LDL cholesterol in the same sample and a reagent kit for use therein.

More specifically, the present invention relates to (1) through (27) below.

(1) A method for quantitatively determining LDL cholesterol in a biological sample, which comprises performing the reaction of cholesterol in the presence of:
a) a biological sample,
b) cholesterol esterase and cholesterol oxidase or cholesterol dehydrogenase (hereinafter collectively referred to as CH enzymes), and
c) a reagent enabling the CH enzymes of b) to act only on LDL cholesterol, and measuring the amount of the hydrogen peroxide or reduced coenzyme formed by the reaction to quantitatively determine the concentration of LDL cholesterol.

(2) The method according to (1), wherein the reagent enabling CH enzymes to act only on LDL cholesterol is a reagent containing at least a polyoxyethylene derivative and a polyoxyethylene-polyoxypropylene copolymer.

(3) The method according to (2), wherein the polyoxyethylene derivative is a polyoxyethylene alkyl ether or a polyoxyethylene alkylaryl ether.

(4) The method according to (2) or (3), wherein the polyoxyethylene-polyoxypropylene copolymer is a surfactant represented by general formula (I):

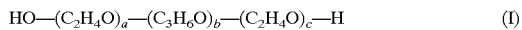

(wherein a, b and c, which may be the same or different, each represents an integer of 1 to 200).

(5) A method for the continuous fractional determination of HDL cholesterol and LDL cholesterol in a biological sample, which comprises subjecting cholesterol to the first reaction in the presence of:
a) a biological sample,
b) CH enzymes, and
c) a reagent enabling the CH enzymes of b) to act only on HDL cholesterol, and measuring the amount of the hydrogen peroxide or reduced coenzyme formed by the first reaction to quantitatively determine the concentration of HDL cholesterol, then adding
d) a reagent enabling the CH enzymes of b) to act only on LDL cholesterol, subjecting cholesterol to the second reaction, and
measuring the amount of the hydrogen peroxide or reduced coenzyme formed by the second reaction to quantitatively determine the concentration of LDL cholesterol.

(6) A method for the continuous fractional determination of HDL cholesterol and LDL cholesterol in a biological sample, which comprises subjecting cholesterol to the first reaction in the presence of:
a) a biological sample,
b) CH enzymes, and
c) a reagent enabling the CH enzymes of b) to act only on HDL cholesterol, and measuring the amount of the hydrogen peroxide or reduced coenzyme formed by the first reaction to quantitatively determine the concentration of HDL cholesterol, then adding
d) CH enzymes, and
e) a reagent enabling the CH enzymes of d) to act only on LDL cholesterol, subjecting cholesterol to the second reaction, and
measuring the amount of the hydrogen peroxide or reduced coenzyme formed by the second reaction to quantitatively determine the concentration of LDL cholesterol.

(7) The method according to (5) or (6), wherein the reagent enabling CH enzymes to act only on LDL cholesterol is a reagent containing at least a polyoxyethylene derivative and a polyoxyethylene-polyoxypropylene copolymer.

(8) The method according to (7), wherein the polyoxyethylene derivative is a polyoxyethylene alkyl ether or a polyoxyethylene alkylaryl ether.

(9) The method according to (7) or (8), wherein the polyoxyethylene-polyoxypropylene copolymer is a surfactant represented by general formula (I):

$$HO-(C_2H_4O)_a-(C_3H_6O)_b-(C_2H_4O)_c-H \qquad (I)$$

(wherein a, b and c, which may be the same or different, each represents an integer of 1 to 200).

(10) A method for the continuous fractional determination of HDL cholesterol and total cholesterol in a biological sample, which comprises
subjecting cholesterol to the first reaction in the presence of:
a) a biological sample,
b) CH enzymes, and
c) a reagent enabling CH enzymes of b) to act only on HDL cholesterol, and
measuring the amount of the hydrogen peroxide or reduced coenzyme formed by the first reaction to quantitatively determine the concentration of HDL cholesterol,
then adding
d) a reagent enabling the CH enzymes of b) to act on cholesterol in all lipoproteins,
subjecting cholesterol to the second reaction, and
measuring the amount of the hydrogen peroxide or reduced coenzyme formed by the second reaction to quantitatively determine the concentration of total cholesterol.

(11) A method for the continuous fractional determination of HDL cholesterol and total cholesterol in a biological sample, which comprises
subjecting cholesterol to the first reaction in the presence of:
a) a biological sample,
b) CH enzymes, and
c) a reagent enabling the CH enzymes of b) to act only on HDL cholesterol, and
measuring the amount of the hydrogen peroxide or reduced coenzyme formed by the first reaction to quantitatively determine the concentration of HDL cholesterol,
then adding
d) CH enzymes, and
e) a reagent enabling the CH enzymes of d) to act on cholesterol in all lipoproteins,
subjecting cholesterol to the second reaction, and
measuring the amount of the hydrogen peroxide or reduced coenzyme formed by the second reaction to quantitatively determine the total cholesterol.

(12) The method according to any one of (5) through (11), wherein the reagent enabling CH enzymes to act only on cholesterol in HDL is a reagent for aggregating lipoproteins other than HDL.

(13) The method according to (12), wherein the reagent for aggregating lipoproteins other than HDL further contains a nonionic surfactant that does not solubilize the aggregated lipoproteins.

(14) The method according to (12) or (13), wherein the reagent for aggregating lipoproteins other than HDL is a reagent comprising heparin or a salt thereof, phosphotungstic acid or a salt thereof, dextran sulfuric acid or a salt thereof, polyethylene glycol, sulfonated cyclodextrin or a salt thereof, sulfonated oligosaccharide or a salt thereof, or a mixture thereof and a divalent metal salt.

(15) The method according to (6) or (11), wherein the CH enzymes used in the first reaction of cholesterol are chemically modified enzymes and the CH enzymes used in the second reaction of cholesterol are enzymes that are not chemically modified.

(16) The method according to any one of (10) through (15), wherein the reagent enabling the CH enzymes to act on cholesterol in all lipoproteins is a reagent containing a lipoprotein solubilizing surfactant.

(17) A reagent for determining LDL cholesterol comprising CH enzymes and a reagent enabling the CH enzymes to act only on LDL cholesterol.

(18) The reagent for determining LDL cholesterol according to (17), wherein the reagent enabling the CH enzymes to act only on LDL cholesterol is a reagent containing at least a polyoxyethylene derivative and a polyoxyethylene-polyoxypropylene copolymer.

(19) The reagent according to (18), wherein the polyoxyethylene derivative is a polyoxyethylene alkylaryl ether.

(20) The reagent according to (18) or (19), wherein the polyoxyethylene-polyoxypropylene copolymer is a surfactant represented by general formula (I):

$$HO-(C_2H_4O)_a-(C_3H_6O)_b-(C_2H_4O)_c-H \qquad (I)$$

(wherein a, b and c, which may be the same or different, each represents an integer of 1 to 200).

(21) A reagent kit for the fractional determination of HDL cholesterol and LDL cholesterol comprising a first reagent and a second reagent, said first reagent comprising a reagent for aggregating lipoproteins other than HDL lipoprotein and a reagent containing CH enzymes, and said second reagent comprising a reagent enabling CH enzymes to act only on LDL cholesterol.

(22) The reagent kit according to (21), wherein the reagent enabling CH enzymes to act only on LDL cholesterol is a reagent containing a polyoxyethylene derivative and a polyoxyethylene-polyoxypropylene copolymer.

(23) The reagent kit according to (21), wherein the polyoxyethylene derivative is a polyoxyethylene alkylaryl ether.

(24) The reagent kit according to (21) or (22), wherein the polyoxyethylene-polyoxypropylene copolymer is a surfactant represented by general formula (I):

$$HO-(C_2H_4O)_a-(C_3H_6O)_b-(C_2H_4O)_c-H \qquad (I)$$

(wherein a, b and c, which may be the same or different, each represents an integer of 1 to 200).

(25) A reagent kit for the fractional determination of HDL cholesterol and total cholesterol comprising a first reagent and a second reagent, said first reagent comprising a reagent for aggregating lipoproteins other than HDL lipoprotein and a reagent containing CH enzymes, and said second reagent comprising a reagent enabling CH enzymes to act on cholesterol in all lipoproteins.

(26) The reagent kit according to (25), wherein the reagent enabling CH enzymes to act on cholesterol in all lipoproteins further contains a lipoprotein solubilizing surfactant.

(27) The reagent kit according to any one of (21) through (26), wherein the reagent for aggregating lipoproteins other than HDL lipoprotein is a reagent comprising heparin or a salt thereof, phosphotungstic acid or a salt thereof, dextran sulfuric acid or a salt thereof, polyethylene glycol, sulfonated cyclodextrin or a salt thereof, sulfonated oligosaccharide or a salt thereof, or a mixture thereof and a divalent metal salt.

Hereinafter the present invention will be described in more detail.

As described above, the present invention relates to a method for the quantitative determination of LDL cholesterol which comprises adding to a biological sample containing various types of lipoproteins a specific reagent enabling CH enzymes to act only on LDL cholesterol (hereinafter referred to as reagent A) and a reagent for use in such a method.

As described above, the present invention also relates to a method for the fractional determination of HDL cholesterol and LDL cholesterol which comprises adding to a biological sample containing various types of lipoproteins a specific reagent enabling CH enzymes to act only on HDL cholesterol (hereinafter referred to as reagent B) to quantitatively determine HDL cholesterol and then adding reagent A to quantitatively determine LDL cholesterol as well as a reagent kit for use therein.

As described above, the present invention further relates to a method for the fractional determination of HDL cholesterol and total cholesterol which comprises adding to a biological sample containing various types of lipoproteins the reagent B to quantitatively determine HDL cholesterol and then adding to the reaction mixture a reagent enabling CH enzymes to act on cholesterol in all lipoproteins (hereinafter referred to as reagent C) to quantitatively determine total cholesterol as well as a reagent kit for use therein.

A biological sample to which the present invention is to be applied is not particularly limited. More specifically, blood itself or blood fractions such as plasma or serum, etc. may be used as the sample.

The reactions for quantitatively determining cholesterol in the present invention are generally carried out in an aqueous medium, preferably in a buffer solution.

Buffers useful in the buffer solution include tris(hydroxymethyl)aminomethane, phosphate buffer, borate buffer and Good's buffer. Examples of Good's buffer are N-(2-acetamido)-2-aminoethanesulfonic acid (ACES), N-(2-acetamido)iminodiacetic acid (ADA), N, N-bis(2-hydroxyethyl)-2-aminoethanesulfonic acid (BES), 3-[N,N-bis(2-hydroxyethyl)amino]-2-hydroxypropanesulfonic acid (DIPSO), N-(2-hydroxyethyl)piperazine-N'-2-ethanesulfonic acid (HEPES), 2-(N-morpholino)ethanesulfonci acid (hereinafter referred to as MES), 3-(N-morpholino)propanesulfonic acid (hereinafter referred to as MOPS), 3-(N-morpholino)-2-hydroxypropanesulfonic acid (MOPSO), piperazine-N,N'-bis(2-ethanesulfonic acid) (hereinafter referred to as PIPES), piperazine-N,N'-bis(2-hydroxypropane-3-sulfonic acid) (POPSO), etc.

The pH of the buffer solution is 5 to 10, preferably 6 to 9. The concentration of the buffer to be used is 5 to 500 mM, preferably 20 to 200 mM.

The reagent A which enables CH enzymes to act only on LDL cholesterol is a reagent that does not enable CH enzymes to act on cholesterol in HDL, VLDL and CM. The reagent A also enables CH enzymes to act only on LDL cholesterol even in the presence of a reagent for aggregating lipoproteins other than HDL, which will be later described.

The reagent A is typically a reagent containing at least a polyoxyethylene derivative and a polyoxyethylene-polyoxypropylene copolymer.

Suitable polyoxyethylene derivative is exemplified by a polyoxyethylene alkylaryl ether, a polyoxyethylene alkyl ether, etc., having the alkyl moiety of at least 8 carbon atoms, e.g., octyl, nonyl, etc. and having the aryl moiety being phenyl, etc.

Specific examples of the polyoxyethylene derivative include commercially available Nonion HS-210, Nonion HS-215, Nonion NS-208.5 and Nonion HS-208 (all produced by NOF Corporation) and Emulgen L-40, Emulgen 911 and Emulgen 810 (all produced by Kao Corporation). The hydrophile-lipophile balance (hereinafter referred to as HLB) of the polyoxyethylene derivative is preferably 9 to 20.

The polyoxyethylene-polyoxypropylene copolymers may be either random copolymers or block copolymers of polyoxyethylene and polyoxypropylene. An example of the copolymer is a compound represented by general formula (I):

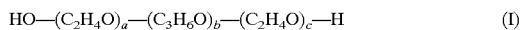

$$HO-(C_2H_4O)_a-(C_3H_6O)_b-(C_2H_4O)_c-H \qquad (I)$$

(wherein a, b and c, which may be the same or different, each represents an integer of 1 to 200).

Examples of the compounds represented by general formula (I) include commercially available compounds such as Pluronic L-121, Pluronic L-122, Pluronic L-101, Pluronic P-103 and Pluronic F-108 (all produced by Asahi Denka Kogyo K. K.). The molecular weight of the polypropylene glycol moiety in the compounds of general formula (I) is preferably at least 2,050, more preferably 2,750 or more, most preferably 3,250 or more. The HLB of the polyoxyethylene-polyoxypropylene copolymers is in preferably 1 to 6.

The respective concentration of the polyoxyethylene derivatives and polyoxyethylene-polyoxypropylene copolymers used is not specifically limited but is preferably 0.001 to 10%, more preferably 0.01 to 5%, most preferably 0.05 to 1%.

Examples of the reagent B that enables CH enzymes to act only on HDL cholesterol are reagents for aggregating lipoproteins other than HDL and antibodies to lipoproteins other than HDL.

Reagents for aggregating lipoproteins other than HDL are generally those containing agents for aggregating these lipoproteins and/or divalent metal salts. Examples of the aggregating agent include heparin or salts thereof, phosphotungstic acid or salts thereof, dextran sulfuric acid or salts thereof, polyethylene glycol, sulfated cyclodextrin or salts thereof, sulfated oligosaccharide or salts thereof, and mixtures thereof. Examples of the cyclodextrin include α-cyclodextrin, β-cyclodextrin and γ-cyclodextrin. Examples of the oligosaccharide include maltotriose, maltotetraose, maltopentaose, maltohexaose and maltoheptaose. Examples of the salts include sodium, potassium, lithium, ammonium and magnesium salts. Examples of the divalent metal salt include magnesium, calcium, manganese and nickel salts.

Preferable examples of the aggregating agent used include 0.02 to 10 mM heparin having a molecular weight of 5, 000 to 20, 000 or salts thereof, 0.1 to 10 mM phosphotungstic acid having a molecular weight of 4,000 to 8,000 or salts thereof, 0.01 to 5 mM dextran sulfuric acid having a molecular weight of 10,000 to 500,000 or salts thereof, 0.1 to 20 mM dextran sulfuric acid having a molecular weight of 1,000 to 10,000 or salts thereof, 0.3 to 100 mM polyethylene glycol (PEG) having a molecular weight of 4,000 to 25,000, 0.1 to 50 mM sulfated cyclodextrin having a molecular weight of 1,000 to 3,000 or salts thereof, 0.1 to 50 mM sulfated oligosaccharide having a molecular weight of 400 to 3,000 or salts thereof, and mixtures thereof. More preferred examples are 0.03 to 1 mM heparin having a molecular weight of 14,000 to 16,000 or salts thereof, 0.1 to 3 mM phosphotungstic acid having a molecular weight of 5,000 to 7,000 or salts thereof, 0.01 to 5 mM dextran sulfuric acid having a molecular weight of 150,000 to 250,000 or salts thereof, 0.1 to 10 mM dextran sulfuric acid having a molecular weight of 1,000 to 5,000 or salts thereof, 1.0 to 50 mM PEG having a molecular weight of 5,000 to 22,000, 0.1 to 10 mM sulfated cyclodextrin having a molecular weight of 1,000 to 2,000 or salts thereof, 0.1 to 10 mM sulfated oligosaccharide having a molecular weight of 400 to 2,000 or salts thereof, and mixtures thereof.

Preferred examples of the divalent metal salt include the salts of magnesium, calcium, manganese, nickel and cobalt, the concentration of which is 0.1 to 50 mM. Preferably, the magnesium salt is used in a concentration of 0.1 to 50 mM.

It is preferred that the agents for aggregating lipoproteins other than HDL further contain a nonionic surfactant that does not dissolve the aggregated lipoproteins.

Examples of the nonionic surfactant that does not dissolve the aggregated lipoproteins include a polyoxyethylene alkyl ether, a polyoxyethylene alkylaryl ether, a polyoxyethylene-polyoxypropylene copolymer, a polyoxyethylene alkyl ether sulfuric acid salts and an alkylbenzene sulfonate. Among these surfactants, polyoxyethylene ethers [Emulgen 220 (Kao Corporation), etc.] are particularly desired as the polyoxyethylene alkyl ether; commercially available Emulgen 66, etc. as the polyoxyethylene alkyl aryl ether; commercially available Pluronic F88 (Asahi Denka Kogyo K. K.) as the polyoxyethylene-polyoxypropylene condensate, commercially available Emal 20C (Kao Corporation) as the polyoxyethylene alkyl ether sodium sulfate, and sodium dodecyl benzenesulfonate as the alkyl benzenesulfonic acid salt.

The nonionic surfactant that does not dissolve the aggregated lipoproteins can be used in combination, so long as the surfactant does not enable CH enzymes to act on LDL cholesterol. However, it is preferable to use the nonionic surfactant solely. The concentration of the nonionic surfactant is not particularly limited but is preferably 0.01 to 10%, more preferably 0.1 to 5%.

Examples of the antibodies to lipoproteins other than HDL include an antiapo-lipoprotein B antibody, an antiapo-lipoprotein C antibody, an antiapo-lipoprotein E antibody and an anti-β-lipoprotein antibody. These antibodies may be employed solely or in combination. The antibodies may be either polyclonal or monoclonal. The antibodies may also be chemically or enzymatically degraded or modified.

As the reagent C enabling CH enzymes to act on cholesterol in all lipoproteins, there are, for example, surfactants that dissolve all lipoproteins.

As the surfactants above, there are used nonionic surfactants that dissolve HDL, LDL, VLDL and CM. Specific examples of such surfactants are nonionic surfactants commercially available as Triton X-100, polyoxyethylene alkyl ethers such as Emulgen 106, Emulgen 108, Emulgen 709, etc. These surfactants may be used solely or in combination. The concentration of the surfactants is not particularly limited but is preferably 0.01 to 10%, more preferably 0.1 to 5%.

As the enzymes having the activities of cholesterol esterase, cholesterol oxidase and cholesterol dehydrogenase which may be used in the present invention, there are, for example, cholesterol esterase and lipoprotein lipase derived from microorganisms or animals having the ability to hydrolyze cholesterol ester, cholesterol oxidase derived from microorganisms having the ability to oxidize cholesterol to produce hydrogen peroxide, and cholesterol dehydrogenase derived from microorganisms or animals.

These enzymes can be employed depending upon specificity to substrate. In the case of the quantitative determination of HDL cholesterol, it is preferred to use an enzyme specific to the cholesterol and for the quantitative determination of LDL cholesterol, an enzyme specific thereto is preferably used. In order to further improve the specificity and stability of these enzymes, enzymes that are chemically modified with a group having polyethylene glycol as a main component, a water-soluble oligosaccharide residue, or a sulfopropyl group may also be used. Furthermore, enzymes obtained by genetic engineering may also be used.

Examples of the reagent for modifying the enzymes (chemical modifier) include compounds wherein polyethylene glycol and a group capable of bonding to an amino group are connected, e.g. Sun Bright VFM4101 (NOF Corporation) wherein polyethylene glycol and a group capable of bonding to an amino group such as N-hydroxysuccinimido group are connected, Sun Bright AKM series, ADM series and ACM series [all manufactured by NOF Corporation, Chemical Engineering Monographs (Kagaku Kogaku Ronbunshu), 20 (3), 459 (1994)] which are compounds having the polyalkylene glycol structure and the acid anhydride structure, compounds wherein a polyethylene glycol-polypropylene glycol copolymer and a group capable of bonding to an amino group are connected, copolymers of polyethylene glycol monomethacryl monomethyl ether and maleic anhydride, etc. Furthermore, activated polyurethane P4000 (Boehringer Mannheim, Directions for Enzyme Modification Set) which is a polyurethane chemical modifier, Dextran T40, which is a dextran chemical modifier, and activated TCT (Boehringer Mannheim, Directions for Enzyme Modification Set), 1,3-propanesultone, etc. may also be used. By the use of these chemical modifiers, the enzymes can be modified with a group having polyethylene glycol as a main component, a group having polypropylene glycol as a main component, a group having a copolymer of polypropylene glycol and polyethylene glycol, a group containing a saccharide in the structure, a sulfopropyl group, a polyurethane group, etc.

A method for the reaction of an enzyme with the above chemical modifier is described in Yuji Inada, "Tanpakushitu-no-Hybrid (Hybrid of Proteins)" published by Kyoritsu Publishing Co. (1987), etc. Typically, when using, e.g., Sun Bright, the enzyme is dissolved in a buffer solution such as HEPES buffer of pH 8 or above, then, e.g., 0.01-500-fold molar amount of Sun Bright is added to the solution at 0° C. to 50° C., followed by stirring for 5 to 60 minutes. The resulting reaction mixture is used as it is, or if necessary, after removal of low molecular weight compounds with ultrafilter.

According to the present invention, the cholesterol esterase, cholesterol oxidase and cholesterol dehydrogenase are preferably used in the reaction mixture at a concentration of 0.01 to 200 U/ml, more preferably 0.1–100 U/ml.

In the present invention, the CH enzymes used to quantitatively determine HDL cholesterol may be used as they are for quantitative determination of LDL cholesterol or cholesterol other than HDL or total cholesterol.

Alternatively, for the quantitative determination of LDL cholesterol or cholesterol other than HDL or total cholesterol, CH enzymes having the same or different specificities may be newly added to the system.

Preferably, chemically modified CH enzymes are used for the quantitative determination of HDL cholesterol and for the determination of cholesterol in lipoproteins other than LDL or HDL or total cholesterol, CH enzymes without any chemical modification are used.

In the reaction of cholesterol according to the present invention, a surfactant or cholic acid which is conventionally used to activate CH enzymes may also be employed as far as they do not affect the reaction specificity. Further, various salts for solubilizing proteins such as globulin may also be used.

As the surfactant for activating the CH enzymes, anionic surfactants are used, e.g., at a concentration of 0 to 1%. Examples of the cholic acid are cholic acid, deoxycholic acid, taurocholic acid and chenodeoxycholic acid. The cholic acid is used at a concentration of 0 to 5%. Examples of the anionic surfactant include an alkyl sulfonate such as 1-pentasulfonate, 1-hexasulfonate, 1-heptasulfonate and 1-octasulfonate. These surfactants are used at a concentration of 0 to 5%.

Examples of the salts include sodium chloride, sodium sulfate, potassium chloride, potassium sulfate, magnesium chloride, magnesium sulfate, magnesium acetate, lithium chloride, lithium sulfate, ammonium chloride, ammonium sulfate, magnesium nitrate and calcium nitrate. These salts are used at a concentration of 0 to 100 mM.

When the reaction of cholesterol is carried out with cholesterol esterase and cholesterol oxidase, hydrogen peroxide is formed. The formed hydrogen peroxide can be quantitatively determined, using e.g. 4-aminoantipyrine and a phenol, 4-aminoantipyrine and Trinder's reagent, or a highly sensitive chromogen in the presence of peroxidase.

Examples of phenols are phenol, 4-chlorophenol, m-cresol and 3-hydroxy-2,4,6-triiodobenzoic acid (HTIB).

Examples of the Trinder's reagents (General Catalog of Dojin Kagaku Kenkyusho, 19th ed., 1994) are anilines such as N-sulfopropylaniline, N-ethyl-N-(2-hydroxy-3-sulfopropyl)-m-toluidine (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-sulfopropyl-m-toluidine (TOPS), N-(2-hydroxy-3-sulfopropyl)-3,5-dimethoxyaniline (HDAOS), N,N-dimethyl-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-(2-hydroxy-3-sulfopropyl)-m-anisidine, N-ethyl-N-(2-hydroxy-3-sulfopropyl)aniline and N-ethyl-N-(2-hydroxy-3-sulfopropyl)-3,5-dimethoxyaniline, N-ethyl-N-(3-methylphenyl)-N'-succinylethylenediamine (EMSE), and N-ethyl-N-(3-methylphenyl)-N'-acetylethylenediamine.

As the highly sensitive chromogen, there are 10-(N-methylcarbamoyl)-3,7-bis(dimethylamino)phenothiadine (MCDP) disclosed in Japanese Published Examined Patent Application No. 33479/85, bis[3-bis(4-chlorophenyl) methyl-4-dimethylaminophenyl]amine (BCMA) disclosed in Japanese Published Examined Patent Application No. 27839/92, the compounds disclosed in Japanese Published Unexamined Patent Application No. 296/87, etc.

The chromogen is preferably used in a concentration of 0.01 to 10 mg/ml.

When the reaction of cholesterol is carried out with cholesterol esterase and cholesterol dehydrogenase in the presence of an oxidized coenzyme, NAD(P), as a substrate, a reduced coenzyme, NAD(P)H, is formed. The formed NAD(P)H can be quantitatively determined by measuring the absorbance of a reaction mixture at 300 to 500 nm, preferably 330 to 400 nm, particularly preferably about 340 nm. The determination of NAD(P)H may otherwise be made by forming a formazan pigment through addition of diaphorase and a tetrazolium salt and then measuring the formazan pigment by colorimetry.

The reaction for the quantitative determination of LDL cholesterol is carried out at 10 to 50° C., preferably 30 to 40° C., usually at 37° C., for 1 to 30 minutes, preferably 2 to 10 minutes.

In the fractional determination, the reaction for quantitatively determining HDL cholesterol (hereinafter referred to as the first reaction) are carried out at 10 to 50° C., preferably 30 to 40° C., usually at 37° C., for 1 to 30 minutes, preferably 2 to 10 minutes; the reactions for quantitatively determining LDL cholesterol or total cholesterol (hereinafter referred to as the second reaction) are carried out at 10 to 50° C., preferably 30 to 40° C., usually at 37° C., for 1 to 30 minutes, preferably 2 to 10 minutes. The start of the second reaction may be at any stage, e.g., after the first reaction is substantially completed or during the first reaction, so long as the quantitative determination of HDL is completed. The second reaction is initiated by adding the reagent A enabling the CH enzymes to act specifically on LDL cholesterol or the reagent C enabling the CH enzymes to act on cholesterol in all lipoproteins and, if necessary, CH enzymes. The hydrogen peroxide or reduced coenzyme [NAD(P)H] thus formed by the second reaction is quantitatively determined using the same reagents as used in the first reaction as they are, or, if necessary and desired, reagents may be newly added to the system.

In the present invention where HDL cholesterol and LDL cholesterol are fractionally determined by first performing the reaction of HDL cholesterol followed by the reaction of LDL cholesterol, the reaction of LDL cholesterol is initiated by adding the reagent A as described above. In this case, when the first reaction of HDL cholesterol is carried out by adding the nonionic surfactant that does not dissolve the aggregated lipoproteins other than HDL, i.e., by adding either the polyoxyethylene derivative or the polyoxyethylene-polyoxypropylene copolymer, the second reaction of LDL cholesterol may also be initiated by adding such a surfactant as forming the reagent A in combination with the surfactant used in the reaction of HDL cholesterol.

The concentration of cholesterol in each lipoprotein is calculated by the following equation based on a difference in absorbance ($\Delta OD$) before and after each reaction using a test sample and a difference in absorbance ($\Delta ODstd$) using a sample with a known concentration of cholesterol in various lipoproteins.

The concentration of LDL cholesterol can be determined by the following equation:

$$\Delta OD \div \Delta ODstd \times (\text{known concentration of } LDL \text{ cholesterol})$$

The concentration of HDL cholesterol can be determined by, e.g., the following equation:

$$\Delta OD \div \Delta ODstd \times (\text{known concentration of } HDL \text{ cholesterol})$$

In the fractional determination, when the compounds formed in the first and second reactions are the same and they are detected by the same method, the concentration of total cholesterol can be calculated according to the following equation, using the difference in absorbance before the first reaction and after the second reaction:

$$\Delta OD \div \Delta ODstd \times (\text{known concentration of total cholesterol})$$

The reagent of the present invention for quantitatively determining LDL cholesterol comprises CH enzymes and a reagent comprising the polyoxyethylene derivative and the polyoxyethylene-polyoxypropylene copolymer. The above reagent for quantitatively determining LDL cholesterol may further contain, if necessary, the aforesaid buffers, reagents for aggregating lipoproteins other than HDL, surfactants used for quantitatively determining cholesterol, cholic acids, various salts, enzymes such as peroxidase, chromogens such as 4-aminoantipyrine and Trinder's reagents or oxidized coenzymes such as NAD(P).

The reagent kit of the present invention for the fractional determination of HDL cholesterol and LDL cholesterol comprises a first reagent and a second reagent. For example, the first reagent comprises a reagent containing an aggregating agent for lipoproteins other than HDL and CH enzymes and the second reagent comprises a reagent containing the polyoxyethylene derivative and the polyoxyethylene-polyoxypropylene copolymer.

The reagent kit of the present invention for the fractional determination of HDL cholesterol and total cholesterol comprises a first reagent and a second reagent. For example, the first reagent comprises a reagent containing an aggregating agent for lipoproteins other than HDL and CH enzymes and the second reagent comprises a reagent containing a non-ionic surfactant that dissolves all lipoproteins (HDL, LDL, VLDL and CM).

The first and second reagents of the reagent kit in accordance with the present invention may further contain, if necessary and desired, the aforesaid buffers, surfactants used for the quantitative determination of cholesterol, cholic acids, various salts, enzymes such as peroxidase, chromogens such as 4-aminoantipyrine and Trinder's reagents, oxidized coenzymes such as NAD(P).

In the second reagent, the source of CH enzymes may be the same as or different from the first reagent. It is preferred that the chemically modified enzyme described above is used as the CH enzyme for the first reagent and a CH enzyme not chemically modified is used as the CH enzyme for the second reagent.

BEST MODES FOR CARRYING OUT THE INVENTION

EXAMPLE 1

Figure 1:
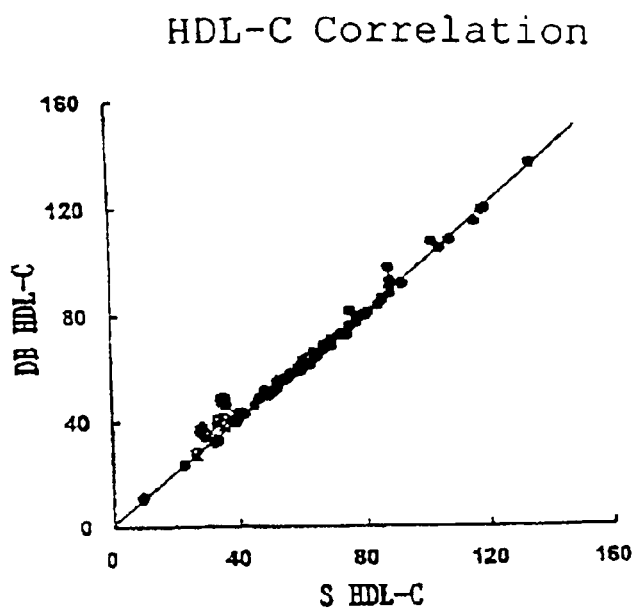
FIG. 1 is a graph showing the correlation between the concentration of HDL cholesterol obtained by the method of the present invention (designated by DB HDL-C in the figure) and the concentration of HDL cholesterol obtained by the comparative method (L HDL-C method, designated by S HDL-C in the figure).

Determination of HDL Cholesterol and LDL Cholesterol

| First reagent (pH = 7) | |
|---|---|
| MES (Nacalai Tesque, Inc.) | 20 mM |
| Dextran sulfonic acid (Tokyo Kasei) | 0.23 mg/ml |
| Magnesium sulfate (Kanto Chemical Co., Ltd.) | 1.5 mg/ml |
| HDAOS (Dojin Kagaku) | 0.23 mg/ml |
| 4-Aminoantipyrine (Saikyo Kasei) | 0.13 mg/ml |
| Polyethylene glycol-modified cholesterol esterase(*1) | 0.25 U/ml |
| Polyethylene glycol-modified cholesterol oxidase(*2) | 1.65 U/ml |
| Peroxidase(Toyobo Co., Ltd.) | 12.5 U/ml |
| Second reagent (pH = 7) | |
| MES (Nacalai Tesque, Inc.) | 20 mM |
| Cholesterol esterase (lipoprotein lipase, Toyobo Co., Ltd.) | 3 U/ml |
| Cholesterol oxidase (Kyowa Hakko Kogyo Co., Ltd.) | 2 U/ml |
| Pulronic L-121 (Asahi Denka Kogyo K.K.) | 0.7% |
| Emulgen L-40 (Kao Corporation) | 0.5% |
| Calcium chloride (Wako Pure Chemical Industries, Ltd.) | 0.1 mg/ml |

(*1): Prepared by dissolving 50 g of cholesterol esterase (Amano Pharmaceutical Co. Ltd.) in 1 L of 0.1 M HEPES buffer (pH 8.5) and adding 330 g of Sun Bright VFM4101 to the solution at 25° C., followed by stirring for 2 hours.
(*2): Prepared by dissolving 50 g of cholesterol oxidase (Kyowa Hakko Kogyo Co., Ltd.) in 1 L of 0.1 M HEPES buffer (pH 8.0) and adding 10 g of Sun Bright VFM4101 to the solution at 15° C., followed by stirring for 2 hours.

Serum samples from 30 healthy subjects were prepared and HDL cholesterol and LDL cholesterol in the samples were determined by the following procedures.

Reagent 1, 2.25 ml, was mixed with 30 μl of the sample. After the mixture was stirred, absorbance E1 was immediately measured at 585 nm. The mixture was then incubated at 37° C. for 5 minutes, and absorbance E2 at the same wavelength was measured. To the reaction solution was added 0.75 ml of Reagent 2. After the mixture was stirred, absorbance E3 was immediately measured at 585 nm and after the mixture was incubated at 37° C. for 5 minutes, absorbance E4 was measured at the same wavelength. Sera having known concentration of cholesterol were treated by substantially the same procedure to measure absorbances E1std, E2std, E3std and E4std, respectively.

The concentration of HDL cholesterol was determined by the following equation, using the absorbance data.

$$(E2-E1) \div (E2std-E1std) \times (\text{known concentration of } HDL \text{ cholesterol})$$

The concentration of LDL cholesterol was likewise determined by the following equation, using the absorbance data.

$$(E4-E3) \div (E4std-E3std) \times (\text{known concentration of } LDL \text{ cholesterol})$$

For comparison, the concentration of HDL cholesterol and LD cholesterol in each serum sample was determined using Determiner L HDL-C and Determiner L LDL-C (both manufactured by Kyowa Medex Co., Ltd.), which are commercial kits for independent determination of the cholesterol, respectively. The coefficient of correlation between the results obtained with these commercial kits and the results according to the method of the present invention was calculated. The coefficient of correlation showed 0.997 for the HDL cholesterol and 0.988 for the LDL cholesterol.

Figure 2:
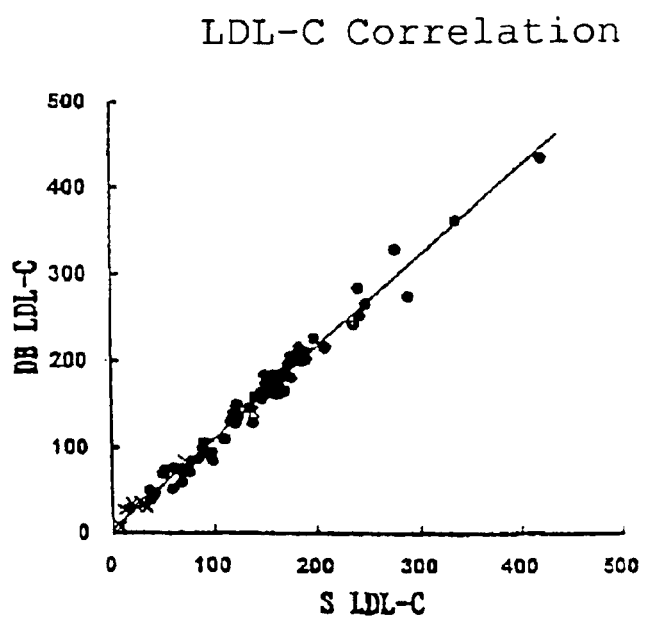
FIG. 2 is a graph showing the correlation between the concentration of LDL cholesterol obtained by the method of the present invention (designated by DB LDL-C in the figure) and the concentration of LDL cholesterol obtained by the comparative method (L LDL-C method, designated by S LDL-C in the figure).

FIG. 1 shows a correlation between the concentration (mg/dL) of HDL cholesterol according to the method of this invention (designated as DB HDL-C in FIG. 1) and the concentration (mg/dL) of HDL cholesterol obtained by the comparative method (L HDL-C method, designated as S HDL-C in FIG. 1). FIG. 2 shows a correlation between the concentration (mg/dL) of LDL cholesterol according to the method of this invention (designated as DB LDL-C in FIG. 2) and the concentration (mg/dL) of LDL cholesterol obtained by the comparative method (L LDL-C method, designated as S LDL-C in FIG. 2).

EXAMPLE 2
Determination of HDL Cholesterol and LDL Cholesterol

| First reagent (pH = 7) | |
| --- | --- |
| MES (Nacalai Tesque, Ltd.) | 20 mM |
| Phosphotungstic acid (Wako Pure Chemical Industries, Ltd.) | 7.5 mg/ml |
| Magnesium sulfate (Wako Pure Chemical Industries, Ltd.) | 1.5 mg/ml |
| TOOS (Dojin Kagaku) | 0.5 mg/ml |
| Emulgen B66 (Kao Corporation) | 10 mg/ml |
| 4-Aminoantipyrine (Saikyo Kagaku) | 0.5 mg/ml |
| Cholesterol esterase (LPBP, Asahi Chemical Industry Co., Ltd.) | 4 U/ml |
| Cholesterol oxidase (rCO, Oriental Yeast Co., Ltd.) | 2 U/ml |
| Peroxidase (Toyobo Co., Ltd.) | 10 U/ml |
| Second reagent (pH = 7) | |
| MES (Nacalai Tesque, Inc.) | 50 mM |
| Cholesterol esterase (lipoprotein lipase, Toyobo Co., Ltd.) | 3 U/ml |
| Cholesterol oxidase (Kyowa Hakko Kogyo Co., Ltd.) | 2 U/ml |
| Pulronic L-121 (Asahi Denka Kogyo K.K.) | 0.7% |
| Emulgen L-40 (Kao Corporation) | 0.5% |
| Calcium chloride (Wako Pure Chemical Industries, Ltd.) | 0.1 mg/ml |

To determine HDL cholesterol and LDL cholesterol, substantially the same procedure as in Example 1 was repeated using the same samples as in Example 1 except that the wavelength measured was changed to 555 nm. The coefficient of correlation between the results obtained with the commercial kits of Determiner L HDL-C and Determiner L HDL-C and the results obtained according to the method of the present invention was calculated. The coefficient of correlation showed 0.929 for the HDL cholesterol and 0.911 for the LDL cholesterol.

EXAMPLE 3
Determination of HDL Cholesterol and Total cholesterol

| First reagent (pH = 7) | |
| --- | --- |
| MES (Nacalai Tesque, Inc.) | 20 mM |
| Dextran sulfonic acid (Tokyo Kasei) | 0.23 mg/ml |
| Magnesium sulfate (Kanto Chemical Co., Ltd.) | 1.5 mg/ml |
| HDAOS (Dojin Kagaku) | 0.23 mg/ml |
| 4-Aminoantipyrine (Saikyo Kasei) | 0.13 mg/ml |
| Polyethylene glycol-modified cholesterol esterase (*1) | 0.25 U/ml |
| Polyethylene glycol-modified | |

-continued

| | |
| --- | --- |
| cholesterol oxidase (*1) | 1.65 U/ml |
| Peroxidase | 12.5 U/ml |
| Second reagent (pH = 6.75) | |
| MES (Nacalai Tesque, Inc.) | 30 mM |
| Triton X-100 (Sigma) | 1 g/L |
| Cholesterol esterase (Toyobo Co., Ltd.) | 2.4 U/ml |
| Cholesterol oxidase (Amano Pharmaceutical Co., Ltd.) | 6.25 U/ml |

(*1): Prepared by the same procedure as *1 in Example 1
(*2): Prepared by the same procedure as *2 in Example 1

Serum samples from 30 healthy subjects used in Example 1 were prepared and HDL cholesterol and LDL cholesterol of the samples were determined by the following procedures.

Reagent 1, 2.25 ml, was mixed with 30 μl of the sample. After the mixture was stirred, absorbance E1 was immediately measured at 585 nm. The mixture was then incubated at 37° C. for 5 minutes, and absorbance E2 was measured at the same wavelength. To the reaction solution was further added 0.75 ml of Reagent 2. After the mixture was stirred, absorbance E3 was immediately measured at 585 nm and after the mixture was incubated at 37° C. for 5 minutes, absorbance E4 was measured at the same wavelength. Separately, sera having known concentration of cholesterol were treated by substantially the same procedure to measure absorbances E1std, E2std, E3std and E4std, respectively.

The concentration of HDL cholesterol was determined by the following equation, using the absorbance data.

$(E2-E1) \div (E2std-E1std) \times$ (known concentration of *HDL* cholesterol)

The concentration of the total cholesterol was also determined by the following equation, using the absorbance data.

$(E4-E1) \div (E4std-E1std) \times$ (known concentration of the total cholesterol)

For comparison, the concentration of HDL cholesterol and the total cholesterol in each serum sample was determined using Determiner L HDL-C and Determiner L TC II (both manufactured by Kyowa Medex Co., Ltd.), which are commercial kits for independent determination of the cholesterol, respectively. The coefficient of correlation between the results obtained with the commercial kits and the results according to the method of the present invention was calculated. The coefficient of correlation showed 0.992 for the HDL cholesterol and 0.999 for the total cholesterol.

Figure 3:
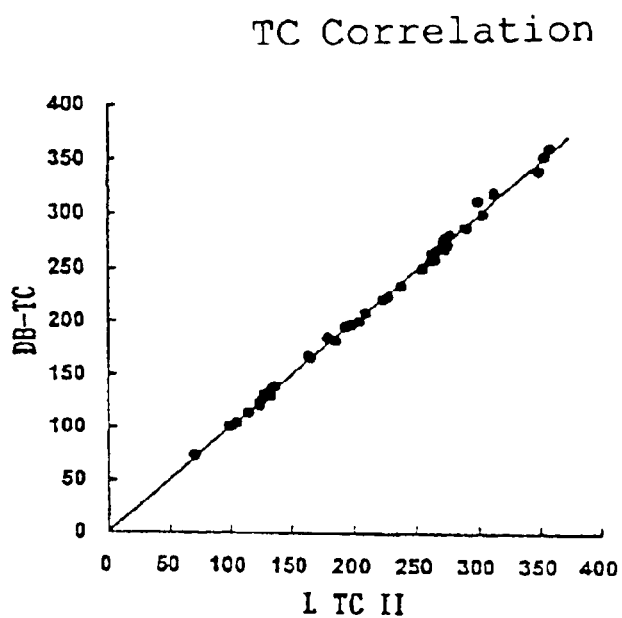
FIG. 3 is a graph showing the correlation between the concentration of total cholesterol obtained by the method of the present invention (designated by DB-TC in the figure) and the concentration of total cholesterol obtained by the comparative method (Determiner L TC II method, designated by L TC II in the figure).

FIG. 3 shows a correlation between the concentration (mg/dL) of the total cholesterol according to the method of this invention (designated as DB-TC in FIG. 3) and the concentration (mg/dL) of the total cholesterol obtained by the comparative method (Determiner L TC II method, designated as L TC II in FIG. 3).

Figure 4:
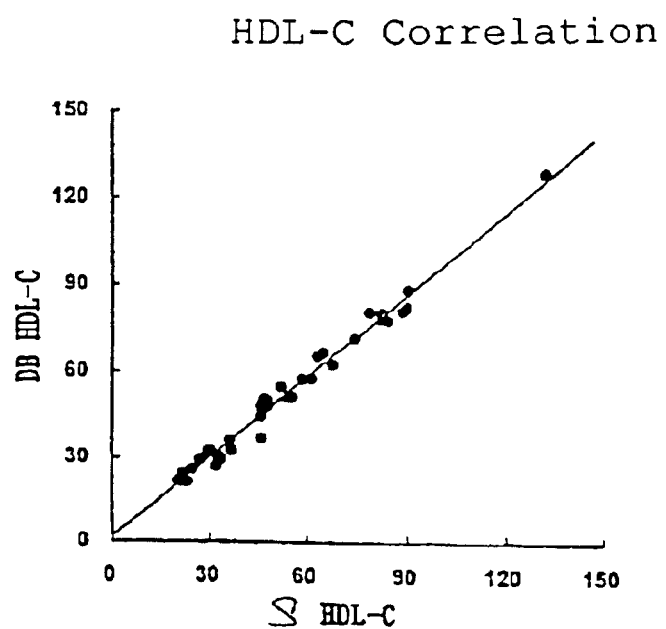
FIG. 4 is a graph showing the correlation between the concentration of HDL cholesterol obtained by the method of the present invention (designated by DB HDL-C in the figure) and the concentration of HDL cholesterol obtained by the comparative method (L HDL-C method, designated by S HDL-C in the figure).

FIG. 4 shows a correlation between the concentration (mg/dL) of HDL cholesterol according to the method of this invention (designated as DB HDL-C in FIG. 4) and the concentration (mg/dL) of HDL cholesterol obtained by the comparative method (L HDL-C method, designated as S HDL-C in FIG. 4).

EXAMPLE 4

| First reagent (pH 7.25) | |
|---|---|
| PIPES (Nacalai Tesque, Inc.) | 50 mM |
| HDAOS (Dojin Kagaku) | 0.3 mg/mL |
| Second reagent (pH 7.25) | |
| PIPES (Nacalai Tesque, Inc.) | 50 mM |
| Cholesterol esterase (lipoprotein lipase, Toyobo Co., Ltd.) | 5 U/mL |
| Cholesterol oxidase (Kyowa Hakko Kogyo Co., Ltd.) | 1 U/mL |
| Peroxidase (Toyobo Co., Ltd.) | 20 U/mL |
| 4-Aminoantipyrine (Saikyo Kasei) | 0.51 mg/mL |
| Calcium chloride (Wako Pure Chemical Industries, Ltd.) | 0.1 mg/mL |
| Surfactant (kind and concentration given in Table 1) | |

As samples, HDL, LDL, VLDL and CM separated from human blood serum by the ultracentrifugation method were used. The respective lipoprotein fractions were provided by Fukushi Iryo Gijutsu Shinkoukai (Welfare Medical Technology Promotion Organization). These fractions were prepared in accordance with Adv. Lipid Res., 6 (1968) [Practical methods for plasma lipoprotein analysis by Hatch, F. & Lees, R.]. The concentration of cholesterol in each lipoprotein used in this test was determined using Determiner L TC II (Kyowa Medex Co., Ltd.). The concentration was found to be 73 mg/dL for HDL, 264 mg/dL for LDL, 84 mg/dL for VLDL and 17 mg/dL for CM.

After 4 μL of each sample was mixed with 300 μL of the first reagent, the mixture was maintained at 37° C. for 5 minutes. At this stage, an absorbance of the mixture was measured. Thereafter, 100 μL of the second reagent was added to the mixture and reacted. After 5 minutes, an absorbance of the reaction mixture was measured. The absorbance was measured at a principal wavelength of 600 nm and a secondary wavelength of 700 nm, using Hitachi 7070 autoanalyzer.

Differences in absorbance obtained before and after the reactions using LDL fraction, HDL fraction, VLDL fraction and CM fraction are shown by $A_{LDL}$, $A_{HDL}$, $A_{VLDL}$ and $A_{CM}$, respectively.

The results are shown in Table 1 in terms of $A_{HDL}/A_{LDL}$, $A_{VLDL}/A_{LDL}$ and $A_{CM}/A_{LDL}$, respectively. The results mean that as the ratio becomes smaller, the conditions for quantitative determination are more specific to LDL.

TABLE 1

| Surfactant | Concentration (%) | $A_{HDL}/A_{LDL}$ | $A_{VLDL}/A_{LDL}$ | $A_{CM}/A_{LDL}$ |
|---|---|---|---|---|
| Pluronic L-121 | 0.2 | 7.3 | 6.6 | 4.6 |
| Emulgen L40 | 0.16 | | | |
| Pluronic L-121 | 0.2 | 9.6 | 13.5 | 3.2 |
| Nonion HS-210 | 0.1 | | | |
| Pluronic L-121 | 0.2 | 10.2 | 7.7 | 1.2 |
| Emulgen 911 | 0.1 | | | |
| Pluronic L-122 | 0.2 | 8.1 | 8.2 | 3.4 |
| Emulgen L40 | 0.16 | | | |
| Pluronic L-121 (comparative example 1) | 0.2 | 34.7 | 47.9 | 16.8 |
| Emulgen L-40 (comparative example 2) | 0.16 | 27.8 | 39.7 | 9.7 |
| Nonion HS-210 (comparative example 3) | 0.1 | 35.5 | 35.5 | 6.1 |
| Nonion HS-215 (comparative example 4) | 0.16 | 76.8 | 33.6 | 4.7 |
| Nonion NS-208.5 (comparative example 5) | 0.24 | 44.5 | 32.4 | 51.2 |
| Nonion NS-208 (comparative example 6) | 0.08 | 30.2 | 47.3 | 28.3 |
| Emulgen 911 (comparative example 7) | 0.1 | 22.6 | 15.9 | 3.0 |
| Emulgen 810 (comparative example 8) | 0.2 | 24.7 | 36.8 | 5.8 |
| Pluronic L-122 (comparative example 9) | 0.2 | 38.1 | 64.1 | 19.0 |

As shown in Table 1, the results reveal that by using the surfactants in combination, the reaction of cholesterol is more specific to LDL cholesterol than the case of using the surfactant alone.

EXAMPLE 5

| First reagent (pH 6.75) | |
|---|---|
| MOPS (Nacalai Tesque, Inc.) | 50 mM |
| HDAOS (Dojin Kagaku) | 0.3 mg/mL |
| Second reagent (pH 6.75) | |
| MOPS (Nacalai Tesque, Inc.) | 50 mM |
| Cholesterol esterase (lipoprotein lipase, Toyobo Co., Ltd.) | 1 U/mL |
| Cholesterol oxidase (Kyowa Hakko Kogyo Co., Ltd.) | 3 U/mL |
| Peroxidase (Toyobo Co., Ltd.) | 20 U/mL |
| 4-Aminoantipyrine (Saikyo Kasei) | 0.51 mg/mL |
| Calcium chloride (Wako Pure Chemical Industries, Ltd.) | 0.1 mg/mL |
| Surfactant (kind and concentration given in Table 2) | |

The test was carried out in a manner similar to Example 4 except for using the surfactants shown in Table 2. $A_{LDL}$, $A_{HDL}$, $A_{VLDL}$ and $A_{CM}$ were thus determined, respectively, based on which the ratios of $A_{HDL}/A_{LDL}$, $A_{VLDL}/A_{LDL}$ and $A_{CM}/A_{LDL}$ were calculated. The concentration of cholesterol in each lipoprotein used in this test was determined using Determiner L TC II (Kyowa Medex Co., Ltd.) and was found to be 81 mg/dL for HDL, 263 mg/dL for LDL, 72 mg/dL for VLDL and 14 mg/dL for CM.

The results are shown in Table 2.

TABLE 2

| Surfactant | Concentration (%) | $A_{HDL}/A_{LDL}$ | $A_{VLDL}/A_{LDL}$ | $A_{CM}/A_{LDL}$ |
|---|---|---|---|---|
| Pluronic L-101 | 0.2 | 8.7 | 7.3 | 2.6 |
| Emulgen L-40 | 0.16 | | | |
| Pluronic P-103 | 0.2 | 13.0 | 3.9 | 1.7 |
| Emulgen L-40 | 0.16 | | | |
| Pluronic F-108 | 0.2 | 15.0 | 4.5 | 1.4 |
| Emulgen L-40 | 0.16 | | | |
| Emulgen L-40 (comparative example 10) | 0.16 | 26.5 | 24.6 | 4.7 |
| Pluronic L-101 (comparative example 11) | 0.2 | 19.0 | 14.3 | 5.6 |
| Pluronic P-103 (comparative example 12) | 0.2 | 24.8 | 3.5 | 1.1 |
| Pluronic F-108 (comparative example 13) | 0.2 | 28.8 | 17.8 | 1.6 |

As shown in Table 2, the results reveal that by using the surfactants in combination, the reaction of cholesterol is more specific to LDL cholesterol than the case of using the surfactant alone.

EXAMPLE 6

| First reagent (pH 6.75) | |
|---|---|
| MOPS (Nacalai Tesque, Inc.) | 20 mM |
| HDAOS (Dojin Kagaku) | 0.3 mg/mL |
| Second reagent (pH 6.75) | |
| MOPS (Nacalai Tesque, Inc.) | 20 mM |
| Cholesterol esterase (lipoprotein lipase, Toyobo Co., Ltd.) | 2 U/mL |
| Cholesterol oxidase (Kyowa Hakko Kogyo Co., Ltd.) | 3 U/mL |
| Peroxidase (Toyobo Co., Ltd.) | 20 U/mL |
| 4-Aminoantipyrine (Saikyo Kasei) | 0.51 mg/mL |
| Calcium chloride (Wako Pure Chemical Industries, Ltd.) | 0.1 mg/mL |
| Surfactant (kind and concentration given in Table 3) | |

The test was carried out in a manner similar to Example 4 except for using the surfactants shown in Table 3. $A_{LDL}$, $A_{HDL}$, $A_{VLDL}$ and $A_{CM}$ were determined, respectively, based on which the ratios of $A_{HDL}/A_{LDL}$, $A_{VLDL}/A_{LDL}$ and $A_{CM}/A_{LDL}$ were calculated. The concentration of cholesterol in each lipoprotein used in this test was determined with Determiner L TC II (manufactured by Kyowa Medex Co., Ltd.) and was found to be 85 mg/dL for HDL, 252 mg/dL for LDL, 75 mg/dL for VLDL and 19 mg/dL for CM.

The results are shown in Table 3.

TABLE 3

| Surfactant | Concentration (%) | $A_{HDL}/A_{LDL}$ | $A_{VLDL}/A_{LDL}$ | $A_{CM}/A_{LDL}$ |
|---|---|---|---|---|
| Pluronic L-121 | 0.7 | 4.0 | 5.0 | 3.4 |
| Emulgen L-40 | 0.5 | | | |

As shown in Table 3, LDL cholesterol can be more specifically determined by using the combination of surfactants.

EXAMPLE 7

| First reagent (pH 7.0) | |
|---|---|
| MOPS (Nacalai Tesque, Inc.) | 10 mM |
| HDAOS (Dojin Kagaku) | 0.3 mg/mL |
| Second reagent (pH 7.0) | |
| MOPS (Nacalai Tesque, Inc.) | 50 mM |
| Cholesterol esterase (lipoprotein lipase, Toyobo Co., Ltd.) | 1 U/mL |
| Cholesterol oxidase (Kyowa Hakko Kogyo Co., Ltd.) | 3 U/mL |
| Peroxidase (Toyobo Co., Ltd.) | 20 U/mL |
| 4-Aminoantipyrine (Saikyo Kasei) | 0.51 mg/mL |
| Calcium chloride (Wako Pure Chemical Industries, Ltd.) | 0.1 mg/mL |
| Surfactant (kind and concentration given in Table 4) | |

The test was carried out in a manner similar to Example 4 except for using the surfactants shown in Table 4. $A_{LDL}$, $A_{HDL}$, $A_{VLDL}$ and $A_{CM}$ were determined, respectively, based on which the ratios of $A_{HDL}/A_{LDL}$, $A_{VLDL}/A_{LDL}$ and $A_{CM}/A_{LDL}$ were calculated. The concentration of cholesterol in each lipoprotein used in this test was determined using Determiner L TC II (Kyowa Medex Co., Ltd.) and was found to be 79 mg/dL for HDL, 273 mg/dL for LDL, 76 mg/dL for VLDL and 16 mg/dL for CM.

The results are shown in Table 4.

TABLE 4

| Surfactant | Concentration (%) | $A_{HDL}/A_{LDL}$ | $A_{VLDL}/A_{LDL}$ | $A_{CM}/A_{LDL}$ |
|---|---|---|---|---|
| Pluronic L-121 | 0.4 | 2.5 | 5.8 | 1.3 |
| Emulgen L-40 | 0.32 | | | |

As shown in Table 4, LDL cholesterol can be determined more specifically by using the combination of the surfactants.

EXAMPLE 8

| First reagent (pH 7.0) | |
|---|---|
| MOPS (Nacalai Tesque, Inc.) | 10 mM |
| HDAOS (Dojin Kagaku) | 0.3 mg/mL |
| Magnesium chloride hexahydrate (Kanto Chemical Co., Ltd.) | 7 mg/dL |
| Sodium dextran sulfate (Tokyo Kasei) | 0.7 mg/dL |
| Second reagent (pH 6.75) | |
| MOPS (Nacalai Tesque, Inc.) | 50 mM |
| Cholesterol esterase (lipoprotein lipase, Toyobo Co., Ltd.) | 1 U/mL |
| Cholesterol oxidase (Kyowa Hakko Kogyo Co., Ltd.) | 3 U/mL |
| Peroxidase (Toyobo Co., Ltd.) | 20 U/mL |
| 4-Aminoantipyrine (Saikyo Kasei) | 0.51 mg/mL |
| Calcium chloride (Wako Pure Chemical Industries, Ltd.) | 0.1 mg/mL |
| Surfactant (kind and concentration given in Table 5) | |

The test was carried out in a manner similar to Example 4 except that the surfactants shown in Table 4 were used and the absorbance was measured immediately after the addition of the second reagent and 5 minutes after the addition of the second reagent to obtain the differences in the absorbance as $A_{LDL}$, $A_{HDL}$, $A_{VLDL}$ and $A_{CM}$, respectively. Based on the differences, the ratios of $A_{HDL}/A_{LDL}$, $A_{VLDL}/A_{LDL}$ and $A_{CM}/A_{LDL}$ were calculated. The concentration of cholesterol in each lipoprotein used in this test was determined using Determiner L TC II (Kyowa Medex Co., Ltd.) and was found to be 79 mg/dL for HDL, 273 mg/dL for LDL, 76 mg/dL for VLDL and 16 mg/dL for CM.

The results are shown in Table 5.

TABLE 5

| Surfactant | Concentration (%) | $A_{HDL}/A_{LDL}$ | $A_{VLDL}/A_{LDL}$ | $A_{CM}/A_{LDL}$ |
|---|---|---|---|---|
| Pluronic L-121 | 0.4 | 2.6 | 4.6 | 1.3 |
| Emulgen L-40 | 0.32 | | | |

As shown in Table 5, LDL cholesterol can be determined more specifically by using the combination of the surfactants.

EXAMPLE 9

| First reagent (pH 7.0) | |
|---|---|
| MOPS (Nacalai Tesque, Inc.) | 10 mM |
| HDAOS (Dojin Kagaku) | 0.3 mg/mL |
| Magnesium chloride hexahydrate (Kanto Chemical Co., Ltd.) | 7 mg/dL |
| Sodium dextran sulfate (Tokyo Kasei) | 0.7 mg/dL |
| Second reagent (pH 7.0) | |
| MOPS (Nacalai Tesque, Inc.) | 50 mM |
| Cholesterol esterase (lipoprotein lipase, Toyobo Co., Ltd.) | 1 U/mL |
| Cholesterol oxidase (Kyowa Hakko Kogyo Co., Ltd.) | 0.6 U/mL |
| Peroxidase (Toyobo Co., Ltd.) | 20 U/mL |
| 4-Aminoantipyrine (Saikyo Kasei) | 0.51 mg/mL |
| Calcium chloride (Wako Pure Chemical Industries Ltd.) | 0.1 mg/mL |
| Surfactant (kind and concentration given in Table 6) | |

The test was carried out in a manner similar to Example 8 except for using the surfactants shown in Table 6. $A_{LDL}$, $A_{HDL}$, $A_{VLDL}$ and $A_{CM}$ were determined, respectively, based on which the ratios of $A_{HDL}/A_{LDL}$, $A_{VLDL}/A_{LDL}$ and $A_{CM}/A_{LDL}$ were calculated. The concentration of cholesterol in each lipoprotein used in this test was determined using Determiner L TC II (Kyowa Medex Co., Ltd.) and was found to be 82 mg/dL for HDL, 270 mg/dL for LDL, 73 mg/dL for VLDL and 14 mg/dL for CM.

The results are shown in Table 6.

TABLE 6

| Surfactant | Concentration (%) | $A_{HDL}/A_{LDL}$ | $A_{VLDL}/A_{LDL}$ | $A_{CM}/A_{LDL}$ |
|---|---|---|---|---|
| Pluronic L-121 | 0.375 | 2.5 | 4.3 | 1.4 |
| Emulgen L-40 | 0.5 | | | |
| Pluronic L-121 | 0.7125 | 2.5 | 2.2 | 1.8 |
| Emulgen L-40 | 0.57 | | | |

As shown in Table 6, LDL cholesterol can be determined more specifically by using the combination of the surfactants.

EXAMPLE 10

| First reagent (pH 7.25) | |
|---|---|
| PIPES (Nacalai Tesque, Inc.) | 50 mM |
| HDAOS (Dojin Kagaku) | 0.3 mg/mL |
| Second reagent (pH 7.25) | |
| PIPES (Nacalai Tesque, Inc.) | 50 mM |
| Cholesterol esterase (lipoprotein lipase, Toyobo Co., Ltd.) | 2 U/mL |
| Cholesterol oxidase (Kyowa Hakko Kogyo Co., Ltd.) | 3 U/mL |
| Peroxidase (Toyobo Co., Ltd.) | 20 U/,L |
| 4-Aminoantipyrine (Saikyo Kasei) | 0.51 mg/mL |
| Calcium chloride (Wako Pure Chemical Industries, Ltd.) | 0.1 mg/mL |
| Emulgen L-40 (Kao Corporation) | 0.16% |
| Pluronic L-121 (Asahi Denka Kogyo K. K.) | 0.2% |

As human serum samples, 88 samples were collected from the patients and provided for the quantitative determination of LDL cholesterol in the samples according to the following procedures.

After 4 µL of each sample was mixed with 300 µL of the first reagent, the mixture was kept at 37° C. for 5 minutes. At this stage, an absorbance of the mixture was measured. Thereafter, 100 µL of the second reagent was added to the mixture and reacted. After 5 minutes, an absorbance of the reaction mixture was measured. Separately, sera with known concentrations of LDL cholesterol were treated, respectively, in the same manner. By measuring an absorbance, the concentration of cholesterol in each sample was quantitatively determined. The absorbance was measured at a principal wavelength of 600 nm and a secondary wavelength of 700 nm, using Hitachi 7070 autoanalyzer.

On the other hand, total cholesterol, HDL cholesterol and neutral fat were measured using Determiner L TC (Kyowa Medex Co., Ltd.), Determiner L HDL-C (Kyowa Medex Co., Ltd.) and Determiner L TG (Kyowa Medex Co., Ltd.), respectively, which are all commercially available kits. Then the concentration of LDL cholesterol was determined in accordance with the following Friedewald formula. A correlation coefficient between the concentration of LDL cholesterol obtained by the method of the present invention and the concentration of LDL cholesterol calculated according to the Friedewald formula was found to be 0.9767.

Friedewald formula:

(concentration of LDL cholesterol) =(concentration of total cholesterol)−(concentration of HDL cholesterol)−(concentration of neutral fat)

Figure 5:
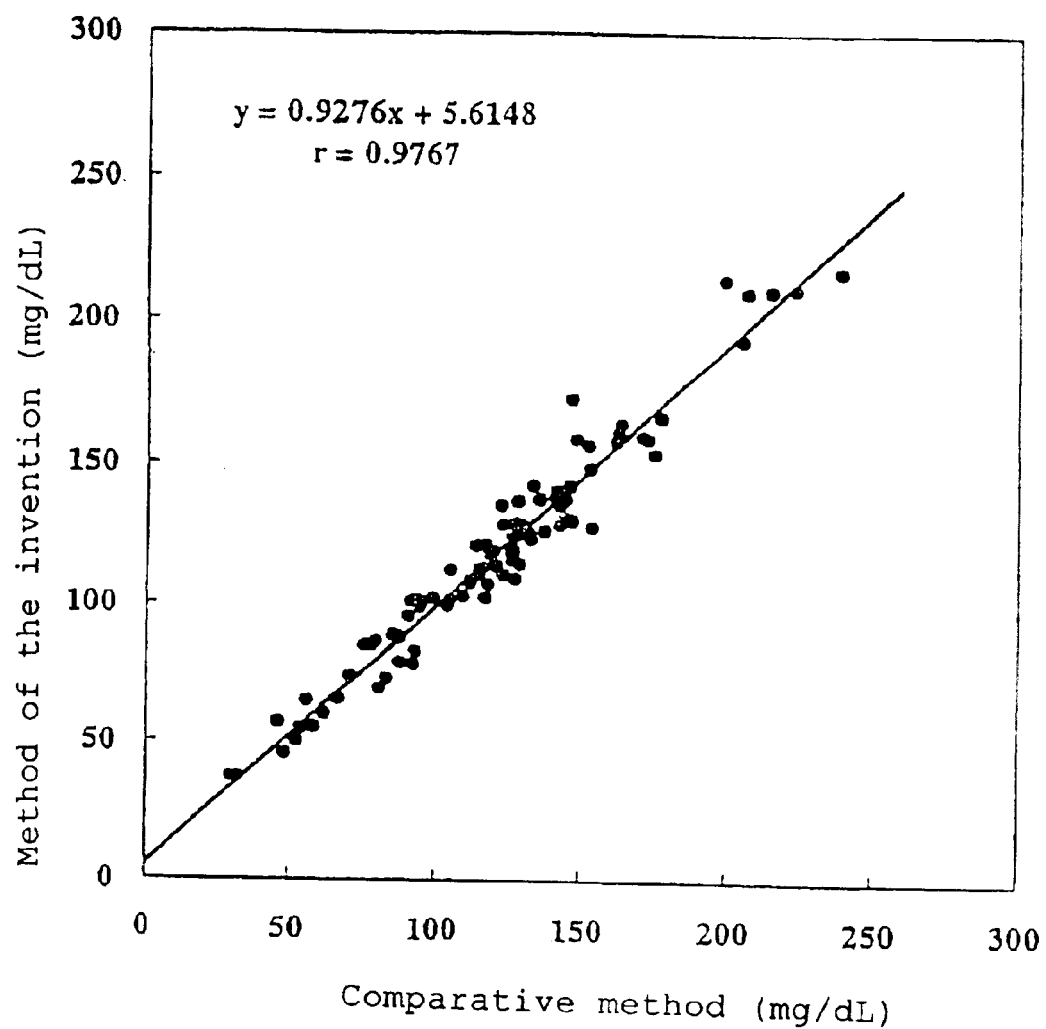
FIG. 5 is a graph showing the correlation between the concentration of LDL cholesterol obtained by the method of the invention (designated by Method of the invention in the figure) and the concentration of LDL cholesterol obtained by the comparative method (designated by Comparative method in the figure) which is calculated in accordance with the Friedewald formula of conversion.

FIG. 5 shows the correlation between the concentration of LDL cholesterol obtained by the method of the invention (designated by Method of the invention in the figure) and the concentration of LDL cholesterol obtained by the comparative method (designated by Comparative method in the figure).

INDUSTRIAL APPLICABILITY

The present invention provides the method for the quantitative determination of LDL cholesterol and the reagent kit for use in the method. The present invention also provides the method for continuous fractional determination of HDL cholesterol and LDL cholesterol or total cholesterol in the same sample in the same system, as well as a reagent kit for use therein.

What is claimed is:

1. A method for quantitatively determining LDL cholesterol in a biological sample, which comprises:
   (I) reacting cholesterol in the presence of:
      a) a biological sample,
      b) CH enzymes selected from the group consisting of (i) a combination of cholesterol esterase and cholesterol oxidase and (ii) a combination of cholesterol esterase, cholesterol dehydrogenase and oxidized coenzyme, and
      c) a polyoxyethylene derivative and a polyoxyethylene-polyoxypropylene copolymer which enable the CH enzymes to act only on LDL cholesterol to form hydrogen peroxide or reduced coenzyme; and
   (II) measuring the amount of the hydrogen peroxide or reduced coenzyme.

2. The method according to claim 1, wherein the polyoxyethylene derivative is a polyoxyethylene alkyl ether or a polyoxyethylene alkylaryl ether.

3. The method according to claim 1, wherein the polyoxyethylene-polyoxypropylene copolymer is a surfactant represented by formula (I):

$$HO-(C_2H_4O)_a-(C_3H_6O)_b-(C_2H_4O)_c-H \quad (I)$$

wherein a, b and c independently represent an integer of 1 to 200.

4. The method according to claim 1, wherein the polyoxyethylene derivative is a polyoxyethylene alkyl ether or a polyoxyethylene alkylaryl ether, and the polyoxyethylene-polyoxypropylene copolymer is a surfactant represented by formula (I):

$$HO-(C_2H_4O)_a-(C_3H_6O)_b-(C_2H_4O)_c-H \qquad (I)$$

wherein a, b and c independently represent an integer of 1 to 200.

5. A method for continuous fractional determination of HDL cholesterol and LDL cholesterol in a biological sample, which comprises:

(I) subjecting cholesterol to reaction in the presence of:
 a) a biological sample,
 b) CH enzymes selected from the group consisting of (i) a combination of cholesterol esterase and cholesterol oxidase and (ii) a combination of cholesterol esterase, cholesterol dehydrogenase and oxidized coenzyme, and
 c) a reagent enabling the CH enzyme to act only on HDL cholesterol to form hydrogen peroxide or reduced coenzyme, (II) measuring an amount of hydrogen peroxide or reduced coenzyme to quantitatively determine the concentration of HDL cholesterol, then adding a polyoxyethylene derivative and a polyoxyethylene-polyoxypropylene copolymer which enable the CH enzymes to act only on LDL cholesterol;

(III) subjecting cholesterol to the reaction to form hydrogen peroxide or reduced coenzyme;

(IV) measuring the amount of the hydrogen peroxide or reduced coenzyme to quantitatively determine the concentration of LDL cholesterol.

6. A method for continuous fractional determination of HDL cholesterol and LDL cholesterol in a biological sample, which comprises:

(I) conducting a first reaction of cholesterol in the presence of:
 a) a biological sample,
 b) CH enzymes selected from the group consisting of (i) a combination of cholesterol esterase and cholesterol oxidase and (ii) a combination of cholesterol esterase, cholesterol dehydrogenase and oxidized coenzyme, and
 c) a reagent enabling the CH enzymes to act only on HDL cholesterol to form hydrogen peroxide or reduced coenzyme, and (II) measuring an amount of hydrogen peroxide or reduced coenzyme to quantitatively determine the concentration of HDL cholesterol, then adding CH enzymes, and a polyoxyethylene derivative and a polyoxyethylene-polyoxypropylene copolymer which enable the CH enzymes to act only on LDL cholesterol, (III) conducting a second reaction of cholesterol to form hydrogen peroxide or reduced coenzyme, and measuring the amount of the hydrogen peroxide or reduced coenzyme to quantitatively determine the concentration of LDL cholesterol.

7. The method according to claim 5 or 6, wherein the polyoxyethylene derivative is a polyoxyethylene alkyl ether or a polyoxyethylene alkylaryl ether.

8. The method according to claim 5 or 6, wherein the polyoxyethylene-polyoxypropylene copolymer is a surfactant represented by formula (I):

$$HO-(C_2H_4O)_a-(C_3H_6O)_b-(C_2H_4O)_c-H \qquad (I)$$

wherein a, b and c, independently represent an integer of 1 to 200.

9. The method according to claim 5 or 6, wherein the reagent enabling CH enzyme to act only on HDL cholesterol is a reagent for aggregating lipoproteins other than HDL.

10. The method according to claim 9, wherein the reagent for aggregating lipoproteins other than HDL is a reagent comprising a divalent metal salt and at least one member selected from the group consisting of heparin or a salt thereof, phosphotungstic acid or a salt thereof, dextran sulfuric acid or a salt thereof, polyethylene glycol, sulfated cyclodextrin or a salt thereof, and sulfated oligosaccharide or a salt thereof.

11. The method according to claim 9, wherein the reagent for aggregating lipoproteins other than HDL further contains a nonionic surfactant that does not solubilize the aggregated lipoproteins.

12. The method according to claim 1, 5 or 6, wherein the CH enzymes are cholesterol esterase and cholesterol oxidase, and the determination of hydrogen peroxide is carried out by reacting the hydrogen peroxide with chromogen in the presence of peroxidase to form a dye and measuring the absorbance of the reaction mixture.

13. The method according to claim 5 or 6, wherein the polyoxyethylene derivative is a polyoxyethylene alkyl ether or a polyoxyethylene alkylaryl ether, and the polyoxyethylene-polyoxypropylene copolymer is a surfactant represented by formula (I):

$$HO-(C_2H_4O)_a-(C_3H_6O)_b-(C_2H_4O)_c-H \qquad (I)$$

wherein a, b and c independently represent an integer of 1 to 200.

14. The method according to claim 5 or 6, wherein the polyoxyethylene derivative is a polyoxyethylene alkyl ether or a polyoxyethylene alkylaryl ether; the polyoxyethylene-polyoxypropylene copolymer is a surfactant represented by formula (I):

$$HO-(C_2H_4O)_a-(C_3H_6O)_b-(C_2H_4O)_c-H \qquad (I)$$

wherein a, b and c independently represent an integer of 1 to 200; and the reagent enabling CH enzymes to act only on HDL comprises a (i) divalent metal salt and (ii) at least one member selected from the group consisting of heparin or a salt thereof, phosphotungstic acid or a salt thereof, dextran sulfuric acid or a salt thereof, polyethylene glycol, sulfated cyclodextrin or a salt thereof, and sulfated oligosaccharide ox a salt thereof.

15. The method according to claim 6, wherein the CH enzymes used in the first reaction are chemically modified enzymes and the CH enzymes used in the second reaction are enzymes that are not chemically modified.

16. A reagent for determining LDL cholesterol comprising CH enzymes selected from the group consisting of (i) a combination of cholesterol esterase and cholesterol oxidase and (ii) a combination of cholesterol esterase, cholesterol dehydrogenase and oxidized coenzyme, and a polyoxyethylene derivative and a polyoxyethylene-polyoxypropylene copolymer which enable the CH enzymes to act only on LDL cholesterol.

17. The reagent according to claim 16, wherein the polyoxyethylene derivative is a polyoxyethylene alkylaryl ether.

18. The reagent according to claim 16, wherein the polyoxyethylene-polyoxypropylene copolymer is a surfactant represented by formula (I):

$$HO-(C_2H_4O)_a-(C_3H_6O)_b-(C_2H_4O)_c-H \quad (I)$$

wherein a, b and c independently represent an integer of 1 to 200.

19. The reagent according to claim 16, wherein the CH enzymes are cholesterol esterase and cholesterol oxidase, and the reagent further comprises peroxidase and chromogen which produces a dye by reaction with hydrogen peroxide in the presence of peroxidase.

20. The reagent according to claim 16, wherein the polyoxyethylene derivative is a polyoxyethylene alkylaryl ether, and the polyoxyethylene-polyoxypropylene copolymer is a surfactant represented by formula (I):

$$HO-(C_2H_4O)_a-(C_3H_6O)_b-(C_2H_4O)_c-H \quad (I)$$

wherein a, b and c independently represent an integer of 1 to 200.

21. A reagent kit for continuous fractional determination of HDL cholesterol and LDL cholesterol comprising a first reagent comprising CH enzymes selected from the group consisting of (i) a combination of cholesterol esterase and cholesterol oxidase and (ii) a combination of cholesterol esterase, cholesterol dehydrogenase and oxidized coenzyme, and a reagent for aggregating lipoproteins other than HDL, and a second reagent comprising a polyoxyethylene derivative and a polyoxyethylene-polyoxypropylene copolymer which enable CH enzymes to act only on LDL cholesterol.

22. The reagent kit according to claim 21, wherein the polyoxyethylene derivative is a polyoxyethylene alkylaryl ether.

23. The reagent kit according to claim 21, wherein the polyoxyethylene-polyoxypropylene copolymer is a surfactant represented by formula (I):

$$HO-(C_2H_4O)_a-(C_3H_6O)_b-(C_2H_4O)_c-H \quad (I)$$

wherein a, b and c independently represent an integer of 1 to 200.

24. The reagent kit according to claim 21, wherein the reagent for aggregating lipoprotein other than HDL is a reagent comprising a divalent metal salt and at least one member selected from the group consisting of heparin or a salt thereof, phosphotungstic acid or a salt thereof, dextran sulfuric acid or a salt thereof, polyethylene glycol, sulfated cyclodextrin or a salt thereof, and sulfated oligosaccharide or a salt thereof.

25. The reagent kit according to claim 21, wherein the second reagent further comprises CH enzymes.

26. The reagent kit according to claim 25, wherein the CH enzymes in the first reagent are chemically modified enzymes and the CH enzymes in the second reagent are enzymes that are not chemically modified.

27. The reagent kit according to claim 21, wherein the CH enzymes are cholesterol esterase and cholesterol oxidase, and the first reagent farther comprises peroxidase and chromogen which produces a dye by reaction with hydrogen peroxide in the presence of peroxidase.

28. The reagent kit according to claim 27, wherein the CH enzymes in the first reagent are chemically modified enzymes and the CH enzymes in the second reagent are enzymes that are not chemically modified.

29. The reagent kit according to claim 21, wherein the reagent for aggregating lipoproteins other than HDL further contains a nonionic surfactant that does not solubilize the aggregated lipoproteins.

30. The reagent kit according to claim 21, wherein the polyoxyethylene derivative is a polyoxyethylene alkylaryl ether, and the polyoxyethylene-polyoxypropylene copolymer is a surfactant represented by formula (I):

$$HO-(C_2H_4O)_a-(C_3H_6O)_b-(C_2H_4O)_c-H \quad (I)$$

wherein a, b and c independently represent an integer of 1 to 200.

31. The reagent kit according to claim 21, wherein the polyoxyethylene derivative is a polyoxyethylene alkylaryl ether; the polyoxyethylene-polyoxypropylene copolymer is a surfactant represented by formula (I):

$$HO-(C_2H_4O)_a-(C_3H_6O)_b-(C_2H_4O)_{c-H} \quad (I)$$

wherein a, b and c independently represent an integer of 1 to 200; and the reagent for aggregating lipoproteins other than HDL comprises (i) a divalent metal salt and (ii) at least one member selected from the group consisting of heparin or a salt thereof, phosphotungstic acid or a salt thereof, dextran sulfuric acid or a salt thereof, polyethylene glycol, sulfated cyclodextrin or a salt thereof, and sulfated oligosaccharide or a salt thereof.

* * * * *

UNITED STATES PATENT AND TRADEMARK OFFICE
CERTIFICATE OF CORRECTION

PATENT NO. : 6,794,157 B1
DATED : September 21, 2004
INVENTOR(S) : Hiroyuki Sugiuchi It is certified that error appears in the above-identified patent and that said Letters Patent is hereby corrected as shown below:

Title page, Item [54] and Column 1, line 2,
Title, "QUATIFICATION" should read -- QUANTIFICATION --.

Title page,
Item [30], Foreign Application Priority Data, "10/264367" should read -- 10-264367 --.

Column 5,
Line 37, "ethanesulfonci" should read -- ethanesulfonic --.

Column 6,
Line 17, "in" should be deleted;
Line 44, "5, 000" should read -- 5,000 --; and
Line 45, "20, 000" should read -- 20,000 --.

Column 8,
Line 22, "propanesultone," should read -- propanesulfone, --; and
Line 64, "1%." should read -- 5%. --.

Column 9,
Line 62, "reaction" should read -- reactions --.

Column 11,
Line 50, "(Determiner L TC II method," should read -- (L TC II method, --.

Column 12,
Line 62, "LD cholesterol" should read -- LDL cholesterol --.

Column 13
Line 48, "L HDL-C" should read -- L LDL-C --.

Column 14,
Line 3, "cholesterol oxidase (*1)" should read --cholesterol oxidase (*2) --;
Line 15, "LDL cholesterol" should read -- total cholesterol --; and
Line 59, "(Determiner L TC II method," should read -- (L TC II method, --.

Column 16,
Line 7, "Nonion NS-208" should read -- Nonion HS-208 --.

UNITED STATES PATENT AND TRADEMARK OFFICE
CERTIFICATE OF CORRECTION

PATENT NO. : 6,794,157 B1
DATED : September 21, 2004
INVENTOR(S) : Hiroyuki Sugiuchi It is certified that error appears in the above-identified patent and that said Letters Patent is hereby corrected as shown below:

Column 20,
Line 67, "HO–$(C_2H_4O)_a$–$(C_3H_6O)_b$–$(C_2H_4O)_{c-H}$" should read -- HO–$(C_2H_4O)_a$–$(C_3H_6O)_b$–$(C_2H_4O)_c$–H --.

Column 21
Line 9, "HO–$(C_2H_4O)_{a-(C_3H_6O)_b}$–$(C_{2H4}O)_{c-H}$" should read -- HO–$(C_2H_4O)_a$–$(C_3H_6O)_b$–$(C_2H_2O)_c$–H --;
Line 35, "coenzyme;" should read -- coenzyme; and --; and
Line 58, "cholesterol," should read -- cholesterol, and --.

Column 22,
Line 6, "c," should read -- c --; and
Line 52, "ox" should read -- or --.

Column 24,
Line 37, "HO–$(C_2H_4O)_a$–$(C_3H_6O)_b$–$(C_2H_4O)_{c-H}$" should read -- HO–$(C_2H_4O)_a$–$(C_3H_6O)_b$–$(C_2H_4O)_c$–H --.

Signed and Sealed this

Tenth Day of May, 2005

JON W. DUDAS
*Director of the United States Patent and Trademark Office*